United States Patent [19] [11] 4,338,317
Temple, Jr. et al. [45] Jul. 6, 1982

[54] PHENOXYETHYL-1,2,4,-TRIAZOL-3-ONE ANTIDEPRESSANTS

[75] Inventors: Davis L. Temple, Jr.; Walter G. Lobeck, Jr., both of Evansville, Ind.

[73] Assignee: Mead Johnson & Company, Evansville, Ind.

[21] Appl. No.: 244,464

[22] Filed: Mar. 16, 1981

[51] Int. Cl.$^3$ .................. C07D 249/00; A61K 31/41; C07D 249/12
[52] U.S. Cl. .................................... 424/250; 544/366
[58] Field of Search ...................... 544/366; 424/250

[56] References Cited

U.S. PATENT DOCUMENTS 3,381,009  4/1968  Palazzo et al. ...................... 544/366
3,857,845  12/1974  Palazzo ............................... 544/366

OTHER PUBLICATIONS

Silvestrini, et al., Int. J. Neuropharmacoc., 1, pp. 587–599, (1968).
Fabre, et al., Current Therapeutic Research, 25 (6), pp. 827–834, (1979).

Primary Examiner—Donald G. Daus
Assistant Examiner—Sharon A. Gibson
Attorney, Agent, or Firm—Robert H. Uloth; Robert E. Carnahan

[57] ABSTRACT

Phenoxyethyl substituted-1,2,4,-triazolones having antidepressant properties typified by 2-[3-[4-(3-chlorophenyl)-1-piperazinyl]propyl]-5-ethyl-4-(2-phenoxyethyl)-2H-1,2,4-triazol-3(4H)-one are disclosed.

9 Claims, No Drawings

PHENOXYETHYL-1,2,4,-TRIAZOL-3-ONE ANTIDEPRESSANTS

BACKGROUND OF THE INVENTION

The present invention relates to 1,2,4-triazole heterocyclic carbon compounds and to their preparation and use. More particularly, the invention relates to 2-[3-[4-(halo-phenyl)-1-piperazinyl]propyl]-5-ethyl-4-(2-phenoxyethyl)-2H-1,2,4-triazol-3(4H)-ones and therapeutic use in treating depression.

U.S. Pat. No. 3,857,845 to G. Palazzo describes the compound 1-[3-(4-meta-chlorophenyl-1-piperazinyl)-propyl]-3,4-diethyl-$\Delta^2$-1,2,4-triazolin-5-one depicted structurally below.

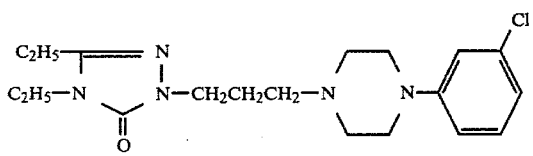

Alternatively, the compound can be named 2-[3-[4-(3-chlorphenyl)-1-piperazinyl]propyl]-4,5-diethyl-2H-1,2,4-triazol-3(4H)-one, and is commonly called etoperidone.

Regarding utility, the '845 Palazzo patent discloses that etoperidone has pharmacological properties typical of tranquilizers including sedation, reduced activity towards the experimentor and lower motor activity. In addition, hypotensive and analgesic activity are reported with possible use as an antianxiety agent and tranquilizer in human therapy mentioned.

U.S. Pat. No. 3,381,009 to G. Palazzo, et al., discloses 1,2,4-triazolo[4,3-a]pyridines of the following general formula

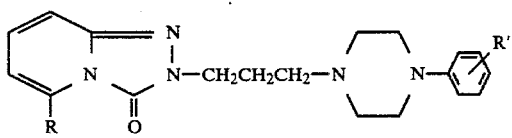

wherein R is hydrogen or methyl and R' is hydrogen, alkyl (1–4C), alkoxy (1–4C), or halogen. The compounds are said to exhibit tranquilizing action, hypotensive action, and analgesic action according to various animal tests. With respect to tranquilizing action, the pharmacological profile includes such behavioral effects as sedation, decrease in motor activity, hypotonia, high dose induced muscular non-coordination and ataxia, and inhibition of conditioned reflexes in the rat. According to the '009 patent, data relative to behavioral, adrenolytic and anti-serotonin effects indicate that the compounds resemble major tranquilizers, such as chlorpromazine more than minor ones such as meprobamate. Pharmacological properties of one compound in particular, 2-[3-[4-(3-chlorophenyl)-1-piperazinyl]-propyl]-1,2,4-triazolo[4,3-a]pyridin-3(2H)-one, have been described in more detail by Silvestrini, et al., International Journal of Neuropharmacology, 7, 587–599 (1968). The aforementioned compound, commonly known as trazodone, has been studied extensively in man and is considered to be an antidepressive equivalent in effectiveness to imipramine but with fewer side effects (Fabre, et al., Current Therapeutic Research, 25, 827–834 (1979)).

SUMMARY OF THE INVENTION AND DESCRIPTION OF PREFERRED EMBODIMENTS

Broadly described, the present invention is concerned with piperazinylalkyl-1,2,4-triazol-3-ones characterized by Formula I

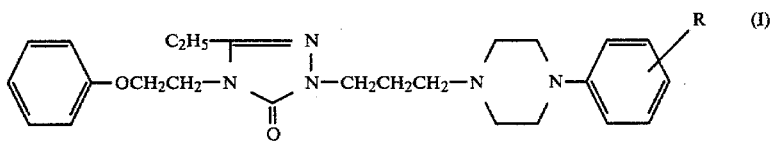

wherein R is halogen and pharmaceutically acceptable salts thereof. The term "halogen" or halo as used herein comprehends fluorine, iodine and most preferably bromine and chlorine.

The pharmaceutically acceptable acid addition salts are those in which the anion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation purposes such as solubility, lack of hygroscopicity, compressibility with respect to tablet formation and compatibility with other ingredients with which the substance may be used for pharmaceutical purposes. The salts are made by reaction of the base of Formula I with the selected acid preferably by contact in solution. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include hydrochloric, hydrobromic, hydroiodic, citric, acetic, benzoic, mandelic, phosphoric, nitric, mucic, isethionic, palmitic, heptanoic, and others.

In its most preferred embodiment, the present invention provides the compound of Formula I wherein R is meta-chloro which is 2-[3-[4-(3-chlorophenyl)-1-piperazinyl]propyl]-5-ethyl-4-(2-phenoxyethyl)-2H-1,2,4-triazol-3(4H)-one (Ia)

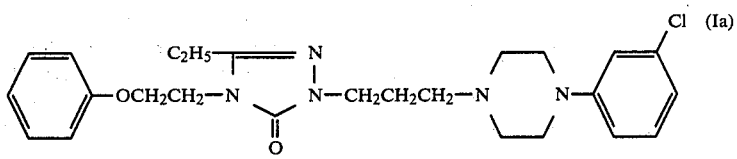

The Formula I compounds are useful pharmacological agents with psychotropic properties. In this regard, they exhibit selective central nervous system effects associated with antidepressant activity according to conventional in vivo test systems such as those listed below.

| Behavioral Test | Reference |
| --- | --- |
| Suppression of conditioned avoidance response (CAR) | Albert, et al., Pharmacologist, 4, 152 (1962). |
| Prevention of reserpine ptosis in mice (antidepressant) | Niemegeers, Industrial Pharmacology, Vol. 2 - Antidepressants, Ed. by S. Fielding and H. Lal, pp. 73–98, Futura, New York, N.Y., (1975). |
| Potentiation of alcohol Hypnois in the mouse (sedative) | — |

In these tests, 2-[3-[4-(3-chlorophenyl)-1-piperazinyl]-propyl]-5-ethyl-4-(2-phenoxyethyl)-2H-1,2,4-triazol-3(4H)-one (Ia) suppressed CAR in the rat and prevented but did not reverse reserpine ptosis in the mouse. Such activity is characteristic of most clinically useful antidepressant agents. Sedation is a common side effect of antidepressants. In this regard, compound Ia exhibited only minimal activity in potentiating alcohol hypnosis in the mouse which is indicative of a relative lack of this adverse reaction.

As further indication of the psychotropic activity and specificity of the instant compounds, state of the art in vitro central nervous system receptor binding methodology can be employed. Certain compounds (commonly referred to as ligands) have been identified which preferentially bind to specific high affinity sites in brain tissue dealing with psychotropic activity or potential for side effects. Inhibition of radiolabeled ligand binding to such specific high affinity sites is considered a measure of a compound's ability to affect corresponding central nervous system function or cause side effects in vivo.

The following tests, as well as others, can be employed in developing a profile of the psychotropic activity of the instant compounds.

| Receptor Binding Assay | Reference |
| --- | --- |
| Dopamine | Burt, et al., Molec. Pharmacol., 12, 800 (1976); Science, 196, 326 (1977); Creese, et al, Science, 192, 481 (1976). |
| Cholinergic | Yamamura, et al., Proc. Natn. Acad. Sci. USA 71 1725 (1974). |
| Alpha-receptor | Crews, et al., Science 202: 322 (1978). Rosenblatt, et al., Brain Res. 160: 186 (1979) U'Prichard, et al., Science 199: 197 (1978). U'Prichard, et al., Molec. Pharmacol. 13: 454 (1977). |
| Serotonin Type 2 | Peroutka and Snyder, Molec. Pharmacol. 16: 687 (1979). |

According to the foregoing assays, Compound Ia inhibits serotonin binding and was relatively inactive with respect to dopamine receptor binding, cholinergic receptor binding, and alpha-receptor binding. The latter is particularly significant in that drugs with high affinity for alpha-receptors relative to serotonin type 2 receptors are likely to cause side effects such as sedation and blood pressure lowering. Thus, the instant compounds and particularly Compound Ia are considered improved antidepressants with minimal side effect potential.

According to the present invention, the piperazinylalkyl-1,2,4-triazol-3-ones characterized by Formula I are obtained by the following process which comprises treating a piperazinylalkyltriazolone of Formula II:

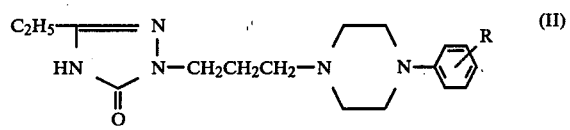

wherein R is halogen attached in the 2, 3 or 4 position of the phenyl ring with a suitable alkali metal base such as sodium hydroxide, potassium hydroxide, sodium carbonate or potassium carbonate to form an alkali metal salt thereof; and then alkylating the Formula II alkali metal salt with phenoxyethyl chloride or phenoxyethyl bromide.

Standard laboratory procedures are employed in carrying out the foregoing reaction such as those described for the alkylation step of the Gabriel synthesis-S. Gabriel, Ber. 20, 2224 (1887). In the present case, the reactants are combined in an inert reaction solvent at temperatures ranging from about 50° C. to 200° C. Acetonitrile and xylene are particularly preferred solvents for carrying out the reaction but other solvents which do not adversely affect the reaction or reactants can be employed. In this regard, solvents such as benzene, toluene dimethylformamide, n-butanol, and the like are suitable. The reaction period varies to some extent depending on solvent and temperature selected. For instance, at lower temperatures, long reaction periods are needed while at higher temperatures, alkylation is completed in a shorter time. In the case of acetonitrile or xylene, optimum yields are obtained with a reaction period of 8 to 68 hours.

A preferred process for preparing Formula I products comprises reacting a piperazinylalkyltriazolone of Formula II with phenoxyethyl bromide or phenoxyethyl chloride in the presence of an alkali metal carbonate such as potassium carbonate or sodium carbonate in acetonitrile.

The Formula II piperazinylalkyltriazolone intermediates are preferably obtained by alkylating hydrazine with a 1-(halophenyl)-4-(3-halopropyl)piperazine to provide a 1-(halophenyl)-4-(3-hydrazinopropyl)piperazine of Formula III:

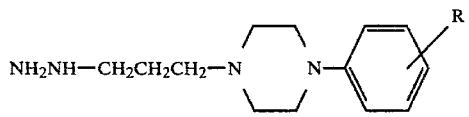 (III)

which is then condensed with N-ethoxycarbonylthiopropionamide

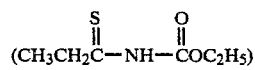
$(CH_3CH_2\overset{S}{\overset{\|}{C}}-NH-\overset{O}{\overset{\|}{C}}OC_2H_5)$ in a reaction inert solvent at elevated temperature. Alkanols, such as ethanol, are particularly preferred as solvents with the reaction conveniently carried out at reflux temperature. Other suitable solvents include acetone, acetonitrile, ethylacetate, dimethylformamide, ethers such as tetrahydrofuran and the like.

Another operable procedure for preparing Formula II intermediates comprises heating N-ethoxycarbonyl-thiopropionamide with hydrazine in ethanol to provide the triazolone compound of Formula IV:

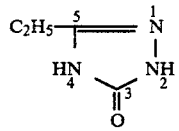 (IV)

which is then alkylated with a 1-(halophenyl)-4-(3-halopropyl)piperazine compound in xylene at reflux temperature. Compared to the previously described preparation of Formula II intermediates, this method is not as satisfactory in that the triazolone (IV) is alkylated indiscriminately at "one, two and four" positions resulting in lower yields of the desired piperazinylalkyltriazolone (II). For example, reaction of triazolone (IV) with 1-(3-phenyl)-4-(3-chloropropyl)piperazine in refluxing xylene affords the following compounds (isolated as hydrochloride salts) as secondary products in addition to the desired Formula (II) piperazinylalkyltriazolone intermediate wherein R is meta-chloro.

Secondary Products

| A = —CH₂CH₂CH₂—N⟨piperazine⟩N—⟨3-chlorophenyl⟩ · HCl | |
|---|---|
| C₂H₅-triazolone-N—A with NH | 1-[3-[4-(3-Chlorophenyl)-1-piperazinyl]-propyl]-5-ethyl-1H-1,2,4-triazol-3(2H)-one hydrochloride; m.p. 210–212° C. (dec.) |
| C₂H₅-triazolone A—N, N—A | 2,4-bis-[3-[4-(3-Chlorophenyl)-1-piperazinyl]-propyl]-5-ethyl-2H-1,2,4-triazol-3(4H)-one hydrochloride; m.p. 206–208° C. (dec.) |

An alternate process for preparing a compound of Formula I comprises condensing a Formula III 1-(halophenyl)-4-(3-hydrazinopropyl)piperazine with N-phenoxyethyl-N-ethoxycarbonylthiopropionamide (Formula V):

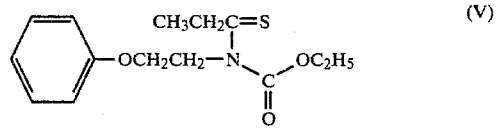 (V)

The condensation is carried out in a suitable reaction inert solvent such as ethanol as previously described for the preparation of the Formula (II) piperazinylalkyltriazolones. The Formula V intermediate can be obtained by standard methods such as condensing methyl dithiopropionate with N-(phenoxyethyl)ethylcarbonate under basic conditions or alkylating N-ethoxycarbonyl-thiopropionamide with phenoxyethyl bromide in the presence of an alkali metal base.

The procedures hereinabove described for preparing Formula I compounds constitutes a unitary process which comprises condensing an amide of the Formula VI:

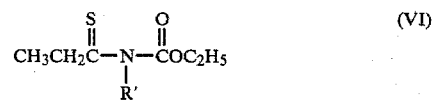 (VI)

wherein R' is hydrogen or phenoxyethyl with a 1-(halophenyl)-4-(3-hydrazinopropyl)piperazine of Formula III:

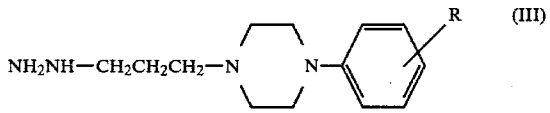 (III)

wherein R is halogen in a reaction inert solvent at elevated temperatures to provide compounds of Formula I when R' is phenoxyethyl and compounds of Formula II when R' is hydrogen and thereafter alkylating a Formula II compound with phenoxyethyl chloride or phenoxyethyl bromide in the presence of an alkali metal base.

Another aspect of the instant invention provides a method for treating a mammal afflicted with depression which comprises administering systemically to said mammal a therapeutically effective antidepressant amount of a compound of Formula I or a pharmaceutically acceptable acid addition salt thereof. An effective dose ranges from 0.01 to 40 mg/kg of body weight with the dosage dependant on effects sought, manner of administration, and to some extent with the particular compound selected. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a smaller quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg. of the active ingredient per unit dose are preferred and are conventionally prepared as tablets, lozenges, capsules, powders, aqueous or oily suspensions, syrups, elixirs and aqueous solutions.

The nature of the pharmaceutical composition employed will, of course, depend on the desired route of administration. For example, oral compositions may be in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

The following non-limiting examples illustrate the process and products of this invention. Nuclear magnetic responance (NMR) spectral characteristics refer to chemical shifts down field ($\delta$) expressed as parts per million (ppm) versus tetramethylsilane as reference standard. The relative area reported for the various shifts corresponds to the number of hydrogen atoms in the individual substituent and the nature of the shifts as to multiplicity is reported as broad singlet (bs), multiplet (m), triplet (t), or quadruplet (q) with coupling constant reported where appropriate. The format is NMR (solvent): $\delta$(relative area, multiplicity, J value). Abbreviations employed are DMSO-$d_6$ (deuterodimethylsulfoxide), IR (infrared), and KBr (potassium bromide).

EXAMPLE 1

2-[3-[4-(3-Chlorophenyl)-1-piperazinyl]propyl]-5-ethyl-1H-1,2,4-triazol-3(2H)-one

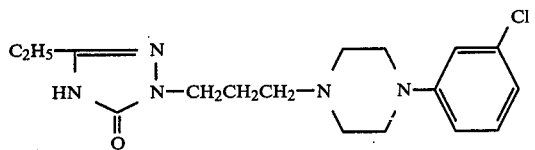

(a) 1-(3-Chloropropyl)-4-(3-chlorphenyl)piperazine Hydrochloride. A 50% sodium hydroxide solution (430.6 g., 5.333 mole) is added dropwise to a stirred solution of 1-(3-chlorophenyl)piperazine hydrochloride (502.0 g., 2.153 mole) and 1-bromo-3-chloropropane (339.0 g., 2.153 mole) in 435 ml. water and 535 ml. acetone while maintaining temperature of 0°-10° C. Stirring is continued for a 16 hr. period at room temperature and the upper organic phase then separated and concentrated under reduced pressure. The remaining residual oil is taken up in 500 ml. acetone, filtered and the filtrate concentrated under reduced pressure to an oily residue which is dissolved in boiling dilute hydrochloric acid (1.67 liter water plus 280 ml. concentrated HCl, 3.36 mole). The oil which initially separates from the cooled acid solution, solidifies on standing and is collected, rinsed with cold water and air dried. Crystallization of this material from water employing activated charcoal affords 438.4 g. (66%) of 1-(3-chloropropyl)-4-(3-chlorophenyl)piperazine hydrochloride, m.p. 196.5°-198.5° C.

(b) 1-(3-Chlorophenyl)-4-(3-hydrozinopropyl)piperazine. Hydrazine hydrate (10.7 g., 0.184 mole) in 20 ml. of ethanol is added slowly to 1-(3-chlorophenyl)-4-(3-chloropropyl)piperazine hydrochloride (9.29 g., 0.03 mole) in 20 ml. of ethanol. After refluxing the mixture for a 3 hr. period, the solvent is removed under reduced pressure and 20 ml. of water added to the residue. A 50 ml. portion of tetrahydrofuran is added to the aqueous mixture which is then saturated with potassium hydroxide pellets employing ice bath cooling. The tetrahydrofuran phase is separated, dried over magnesium sulfate and concentrated under reduced pressure to afford 7.4 g. (92%) of 1-(3-chlorophenyl)-4-(3-hydrazinopropyl)-piperazine employed without further purification in the following step.

(c) 2-[3-[4-(3-Chlorophenyl)-1-piperazinyl]propyl]-5-ethyl-1H-1,2,4-triazol-3(2H)-one. A solution of 1-(3-chlorophenyl)-4-(3-hydrazinopropyl)piperazine (19.6 g., 0.073 mole) in 90 ml. of ethanol is added to N-ethoxycarbonylthiopropionamide (12.13 g., 0.073 mole) in 30 ml. of ethanol. The mixture is refluxed for a 16 hr. period with evolution of hydrogen sulfide and then concentrated under reduced pressure. Crystallization of residual material from ethanol affords 18.3 g. (72%) of 2-[3-[4-(3-chlorophenyl)-1-piperazinyl]propyl]-5-ethyl-1H-1,2,4-triazol-3(2H)-one, m.p. 79°-81° C.

Addition of ethanolic hydrogen chloride to a sample of the base in ethanol with precipitation of the salt with ether affords 2-[3-[4-(3-chlorophenyl)-1-piperazinyl]-propyl]-5-ethyl-1H-1,2,4-triazol-3(2H)-one hydrochloride, m.p. 165°-167° C.

Anal. Calcd. for $C_{17}H_{24}ClN_5O \cdot HCl$: C, 52.86; H, 6.53; N, 18.13. Found: C, 52.72; H, 6.44; N, 17.96.

NMR (DMSO-$d_6$): 1.15 (3H,t, 7.3 Hz), 2.16 (2H,m), 2.43 (2H,q, 7.3 Hz), 3.18 (8H,m), 3.68 (4H,m), 6.89 (3H,m), 7.24 (1H,m), 11.49 (1H,bs).

IR (0.5% KBr, cm$^{-1}$): 770, 940, 1255, 1440, 1485, 1595, 1690, 2570, 2980.

EXAMPLE 2

2-[3-[4-(3-Chlorophenyl)-1-piperazinyl]propyl]-5-ethyl-4-(2-phenoxyethyl)-2H-1,2,4-triazol-3(4H)-one Hydrochloride

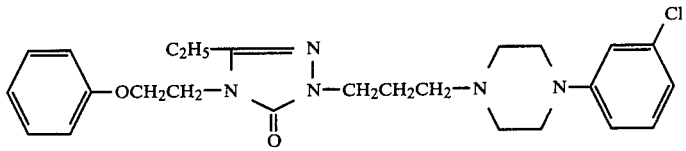

(a) Reaction in Xylene.

Sodium hydroxide (2.08 g., 0.052 mole) in 10 ml. of water is added slowly to 2-[3-[4-(3-chlorophenyl)-1-piperazinyl]propyl]-5-ethyl-1H-1,2,4-triazol-3(2H)-one (18.2 g., 0.052 mole) in 150 ml. of warm ethanol with stirring. When mixing is complete, distillables are removed under reduced pressure. Ethanol is added to residual material and removed under reduced pressure and the process repeated until the sodium salt of 2-[3-[4-(3-chlorophenyl)-1-piperazinyl]propyl]-5-ethyl-1H-1,2,4-triazol-3(2H)-one is obtained as a hard solid.

The sodium salt is pulverized, suspended in 200 ml. of xylene and mixed with phenoxyethyl bromide (10.4 g., 0.052 mole) in 20 ml. of xylene. The resulting mixture is refluxed with stirring for a 64 hr. period and the hot reaction mixture filtered. The filtrate is concentrated under reduced pressure and residual material taken up in ether. Insolubles are collected and the ether filtrate concentrated to afford 22.9 g. (94%) of 2-[3-[4-(3-chlorophenyl)-1-piperazinyl]propyl]-5-ethyl-4-(2-phenoxyethyl)-2H-1,2,4-triazol-3(4H)-one as the free base. Purification of the product is carried out by acidifying a solution of the free base in ethanol with ethanolic hydrogen chloride, and crystallization to afford hydrated (0.25 mole) 2-[3-[4-(3-chlorophenyl)-1-piperazinyl]propyl]-5-ethyl-4-(2-phenoxyethyl)-2H-1,2,4-triazol-3(4H)-one hydrochloride, m.p. 175°–177° C. (30.7% yield).

Anal. Calcd. for $C_{25}H_{32}ClN_5O_2 \cdot HCl \cdot \frac{1}{4}H_2O$: C, 58.77; H, 6.61; N, 13.71. Found: C, 58.61; H, 6.48; N, 13.68.

NMR (DMSO-$d_6$): 1.20 (3H,t, 7.5 Hz), 2.16 (2H,m), 2.66 (2H,q, 7.5 Hz), 3.27 (8H,m), 3.74 (4H,m), 3.96 (2H,t), 4.17 (2H,t), 6.96 (6H,m), 7.29 (3H,m), 11.50 (1H,bs).

IR (0.5% KBr, cm$^{-1}$): 755, 940, 1235, 1440, 1490, 1595, 1710, 2580, 2940.

A sample of non-hydrated 2-[3-[4-(3-chlorophenyl)-1-piperazinyl]propyl]-5-ethyl-4-(2-phenoxyethyl)-2H-1,2,4-triazol-3(4H)-one hydrochloride obtained according to the above process melted at 175°–177° C.

Anal. Calcd. for $C_{25}H_{32}ClN_5O_2 \cdot HCl$: C, 59.29; H, 6.57; N, 13.83. Found: C, 58.98; H, 6.44; N, 13.58.

NMR (DMSO-$d_6$): 1.20 (3H,t, 7.5 Hz), 2.14 (2H,m), 2.65 (2H,q, 7.5 Hz), 3.25 (8H,m), 3.72 (4H,m), 3.95 (2H,t), 4.16 (2H,t), 6.91 (6H,m), 7.25 (3H,m), 11.61 (1H,bs).

$C^{13}$NMR (DMSO-$d_6$): 9.65, 18.40, 22.90, 40.57, 41.89, 44.73, 50.31, 52.92, 64.95, 114.06, 114.30, 115.21, 119.12, 120.93, 129.53, 130.55, 133.94, 147.92, 150.78, 153.15, 157.87.

IR (0.5% KBr, cm$^{-1}$): 750, 940, 1235, 1440, 1485, 1595, 1710, 2570, 2930.

(b) Reaction in Acetonitrile With Potassium Carbonate.

A mixture of 2-[3-[4-(3-chlorophenyl)-1-piperazinyl]propyl]-5-ethyl-1H-1,2,4-triazol-3(2H)-one (15 g., 0.043 mole), phenoxyethyl bromide (8.62 g., 0.043 mole) and potassium carbonate (11.9 g., 0.086 mole) and a trace of potassium iodide in 100 ml. of acetonitrile is refluxed for a 64 hr. period. The reaction mixture is filtered, the filtrate concentrated under reduced pressure and residual material taken up in ether and filtered. Concentration of the ethereal filtrate affords 18.35 g. (91%) of the free base product 2-[3-[4-(3-chlorophenyl)-1-piperazinyl]propyl]-5-ethyl-4-(2-phenoxyethyl)-2H-1,2,4-triazol-3(4H)-one. The free base is converted to the hydrochloride in ethanol employing ethanolic hydrogenchloride and crystallized from ethanol to afford a 53% yield of analytically pure 2-[3-[4-(3-chlorophenyl)-1-piperazinyl]propyl]-5-ethyl-4-(2-phenoxyethyl-2H-1,2,4-triazol-3(4H)-one hydrochloride, m.p. 175°–177° C.

Anal. Calcd. for $C_{25}H_{32}ClN_5O_2 \cdot HCl$: C, 59.29; H, 6.57; N, 13.83. Found: C, 59.42; H, 6.68; N, 13.52.

NMR (DMSO-$d_6$): 1.20 (3H,t, 7.5 Hz), 2.15 (2H,m), 2.65 (2H,q, 7.5 Hz), 3.25 (8H,m), 3.72 (4H,m), 3.95 (2H,t), 4.16 (2H,t), 6.93 (6H,m), 7.27 (3H,m), 11.61 (1H,bs).

IR (0.5% KBr, cm$^{-1}$): 755, 940, 1240, 1440, 1490, 1595, 1710, 2580, 2940.

What is claimed is:

1. A compound of Formula I

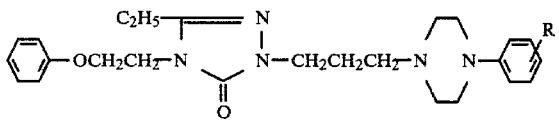

wherein R is halogen or a pharmaceutically acceptable acid addition salt thereof.

2. The compound of claim 1 which is 2-[3-[4-(3-chlorophenyl)-1-piperazinyl]propyl]-5-ethyl-4-(2-phenoxyethyl)-2H-1,2,4-triazol-3(4H)-one.

3. The compound of claim 1 which is 2-[3-[4-(3-chlorophenyl)-1-piperazinyl]propyl]-5-ethyl-4-(2-phenoxyethyl)-2H-1,2,4-triazol-3(4H)-one hydrochloride.

4. The method for treating a mammal afflicted with depression comprising administering to said mammal a therapeutically effective antidepressant amount of a compound of claim 1 or a pharmaceutically acceptable acid addition salt thereof.

5. The method of claim 4 wherein the compound is 2-[3-[4-(3-chlorophenyl)-1-piperazinyl]propyl]-5-ethyl-4-(2-phenoxyethyl)-2H-1,2,4-triazol-3(4H)-one.

6. The method of claim 4 wherein the compound is 2-[3-[4-(3-chlorophenyl)-1-piperazinyl]propyl]-5-ethyl-4-(2-phenoxyethyl)-2H-1,2,4-triazol-3(4H)-one hydrochloride.

7. The pharmaceutical composition comprising an antidepressant amount of a compound of claim 1 or a pharmaceutically acceptable acid addition salt thereof and a pharmaceutically acceptable carrier.

8. The pharmaceutical composition of claim 7 wherein the compound is 2-[3-[4-(3-chlorophenyl)-1-piperazinyl]propyl]-5-ethyl-4-(2-phenoxyethyl)-2H-1,2,4-triazol-3(4H)-one.

9. The pharmaceutical composition of claim 7 wherein the compound is 2-[3-[4-(3-chlorophenyl)-1-piperazinyl]propyl]-5-ethyl-4-(2-phenoxyethyl)-2H-1,2,4-triazol-3(4H)-one hydrochloride.

* * * * *

UNITED STATES PATENT AND TRADEMARK OFFICE

CERTIFICATE EXTENDING PATENT TERM
UNDER 35 U.S.C. § 156

PATENT NO.    :   4,338,317

ISSUED        :   July 6, 1982

INVENTOR(S)   :   Davis L. Temple, Jr. et al.

PATENT OWNER :   Mead Johnson & Company

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

TWO YEARS from the original expiration date of the patent, March 16, 2001, with all rights pertaining thereto as provided by 35 U.S.C. § 156(b).

I have caused the seal of the Patent and Trademark Office to be affixed this 31st day of May 1996.

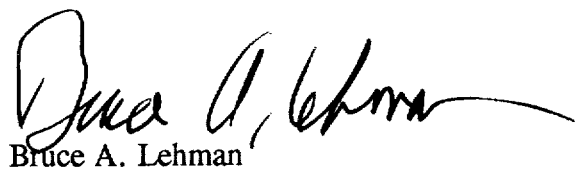

Bruce A. Lehman
Assistant Secretary of Commerce and
Commissioner of Patents and Trademarks